US00PP15502P2

(12) United States Plant Patent
Olesen et al.

(10) Patent No.: US PP15,502 P2
(45) Date of Patent: Jan. 25, 2005

(54) CLIMBING ROSE PLANT NAMED 'POULYC004'

(50) Latin Name: *Rosa hybrida*
Varietal Denomination: POULyc004

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/719,711

(22) Filed: Nov. 21, 2003

(51) Int. Cl.[7] ..... A01H 5/00
(52) U.S. Cl. ..... Plt./111
(58) Field of Search ..... Plt./111, 112, 109

*Primary Examiner*—Anne Marie Grunberg
*Assistant Examiner*—June Hwu

(57) ABSTRACT

A new climbing garden rose plant which has abundant, deep yellow flowers and attractive foliage. This new and distinct variety has shown to be uniform and stable in the resulting generations from asexual propagation.

1 Drawing Sheet

Botanical classification: *Rosa hybrida.*

Variety denomination: 'POULyc004'.

SUMMARY OF THE INVENTION

The present invention constitutes a new and distinct variety of garden rose plant which originated from a controlled crossing between an unnamed female parent plant and an unnamed male parent plant. The two parents were crossed during the summer of 1991, and the resulting seeds were planted in a controlled environment in Fredensborg, Denmark. The new variety is named 'POULyc004'.

The new variety may be distinguished from its pollen parent, by the following combination of characteristics:

1. While the pollen parent has a free branching, low growing growth habit, 'POULyc004' has a climbing growth habit.
2. While the pollen parent has very double flowers, 'POULyc004' has flowers characterized as double.

The new variety may be distinguished from its unnamed seed parent, by the following combination of characteristics:

1. The seed parent is multiflorus with up to approximately 20 flowers per stem. 'POULyc004' has up to 5 flowers per stem.
2. While the seed parent has no fragrance, 'POULyc004' has a light floral scent.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Disease resistance.
4. Improved flowering habit. Since the variety is less apically dominant, flowers are produced from lower branches to the top.

This combination of qualities is not present in previously available commercial cultivars of this type, known to the inventor, and distinguish 'POULyc004' from all other varieties of which we are aware.

As part of their rose development program, L. Pernille Olesen and Mogens N. Olesen germinated the seeds from the aforementioned hybridization during winter 1991 and conducted evaluations on the resulting seedlings in a controlled environment in Fredensborg, Denmark.

'POULyc004' was selected in the spring 1992 by the inventors as a single plant from the progeny of the aforementioned hybridization.

Asexual reproduction of 'POULyc004' by traditional budding and rooted cuttings was first done by L. Pernille and Mogens N. Olesen in their nursery in Fredensborg, Denmark in June, 1992. This initial and other subsequent asexual propagations conducted in controlled environments have demonstrated that the characteristics of 'POULyc004' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULyc004'. Specifically illustrated in FIG. 1:

FIG. 1.1; Open flower, stem showing open flower, the attachment of buds, and peduncles;

FIG. 1.2; Flower bud closed, partially open bloom and open flower.

FIG. 1.3; Flower petals, detached;

FIG. 1.4; Sepals, receptacle, and pedicel;

FIG. 1.5; Mature leaves;

FIG. 1.6; Bare stems.

DETAILED DESCRIPTION OF THE VARIETY

The following is a description of 'POULyc004', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULhult', a rose variety from the same inventors described and illustrated in U.S. Plant patent application Ser. No. 10/267,547 and dated Oct. 8, 2002, are compared to 'POULyc004' in Chart 1.

CHART 1

| | 'POULyc004' | 'POULhult' |
|---|---|---|
| Flower Diameter | 30–35 mm. | 55 to 60 mm. |
| Color of outermost petals after opening inner side. | Yellow Group 13A. | Yellow Group 11D. |
| Petal Size | 16 mm (l) × 10 mm (w). | 27 mm (l) × 28 mm (w). |

Parents:

*Seed parent.*—Unnamed plant.

*Pollen parent.*—Unnamed plant.

FLOWER AND FLOWER BUD

Blooming habit: Continuous.

Flower bud:

*Size.*—Upon opening, 11 mm in length from base of receptacle to end of bud. Bud diameter is 6 mm.

*Bud form.*—Pointed ovoid.

*Bud color.*—As sepals unfold, petals are Yellow-Orange Group 15B to 15C. Yellow-Orange Group 15B to 15C. at ¼ opening. Sepals: Upper surface: Color: Yellow-Green Group 146C with intonations of Greyed-Purple Group 183A. Lower surface: Color: Yellow-Green Group 144A with intonations of Greyed-Purple Group 183A. Shape: Subulate. Margins: Margins have weak foliaceous appendages on three of the five sepals. Surfaces of sepals moderately pubescent. Stipitate glands observed at the margins and the apex of sepals in sparse quantity. Anthocyanin: Weak. Greyed-Purple Group 183A. Size: 20 mm long by 4 mm wide.

*Receptacle.*—Surface texture: Smooth and glaucous. Shape: Urn-shaped. Size: 50 mm (h)×5 mm (w). Color: Yellow-Green Group 144A.

*Peduncle.*—Length: Normally 10 to 15 cm from base of the branch to flowering portion. Diameter: 2.5 mm. Color: Yellow Green 144A.

*Pedicel.*—Surface: Smooth, slightly glabrous. Length: 23 to 25 mm average length. Diameter is normally 2 mm.

*Borne.*—Multiples of 5 buds per flowering stem. Occasionally single.

*Anthocyanin.*—Color: Greyed-Red Group 183A.

Flower bloom:

*Fragrance.*—Light floral.

*Duration.*—The blooms have a duration on the plant of approximately 7 to 10 days.

*Size.*—Average flower diameter is 30–35 mm when open.

*Form.*—Rosette with outermost petals slightly overlapping. Shape of flower when viewed from the side: Upon opening, upper part: Flattened convex. Upon opening, lower part: Flat. Open flower, upper part: Flattened convex. Open flower, lower part: Flat.

*Petalage.*—Semi-double. Average range: 25–30 petals under normal conditions with 3 petaloids.

Color:

*Upon opening, petals.*—Outermost petals: Outer side: Yellow Group 13B. Occasionally, outer surface of outer petals exhibit splotches of White Group 155A. Inner side: Yellow Group 13A. Innermost petals: Outer side: Yellow Group 13B. Inner side: Yellow Group 13A.

*Upon opening, basal petal spots.*—No distinctive coloration at petal base observed.

*After opening, petals.*—Outermost petals: Outer side: Yellow Group 13B. Occasionally, outer surface of outer petals exhibit splotches of White Group 155A. Inner side: Yellow Group 13A. Innermost petals: Outer side: Yellow Group 13B. Inner side: Yellow Group 13A.

*After opening, basal petal spots.*—No distinctive coloration at petal base observed.

General tonality: On open flower Yellow Group 13A to 13B. No change in the general tonality at the end of the $10^{th}$ day. Afterwards, general tonality is Yellow Group 12C.

Petals:

*Petal reflex.*—Petals reflexed slightly.

*Margin.*—Entire with point in center of margin.

*Shape.*—Apex: Pointed. Base: Acute.

*Size.*—16 mm (l)×10–15 mm (w).

*Texture.*—Smooth.

*Thickness.*—Thin.

*Arrangement.*—Not formal.

Petaloids:

*Quantity.*—3–5.

*Size.*—12 mm (l)×7 mm (w).

*Color.*—Upper surface: Yellow Group 13A. Lower surface: Yellow Group 13A.

Reproductive organs:

*Pistils.*—Length: 5–6 mm long. Quantity: 35 (actual count).

*Pollen.*—None observed.

*Anthers.*—Size: 1.5 mm long. Color: Yellow-Orange Group 18A. Quantity: 48 (actual count).

*Filaments.*—Color: Orange Group 17B. Length: 5–6 mm.

*Stigmas.*—Level in location to anthers. Color: Yellow-Green Group 145D.

*Styles.*—Color: Yellow-Green Group 145D. Other intonations: None.

*Hips.*—None observed in the field nursery in Jackson County Oreg.

PLANT

*Plant growth.*—Vigorous climbing habit with weak apical dominance in flowering characteristics.

Stems:

*Color.*—Young wood: Yellow-Green Group 144A to 144B. Older wood: Yellow-Green Group 144A to 144B.

*Surface texture.*—Young wood: Smooth. Older wood: Rough.

*Thorns.*—Incidence: 4 thorns per 10 cm of stem. Size: Average length: 4 mm. Juvenile Thorn Color: Greyed-Purple Group 183A to 183B. Mature Thorn Color: Greyed-Purple Group 183B. Shape: Linear to concave.

*Anthocyanin.*—None observed.

Plant foliage: Normal number of leaflets on normal leaves in middle of the stem: 5 leaflets.

*Compound leaf size.*—12–30 mm (l)×7–20 mm (w).

*Color.*—Mature foliage: Upper leaf surface: Yellow-Green Group 147A. Lower leaf surface: Yellow-Green Group 146A to 146B. Juvenile foliage: Upper leaf surface: Yellow-Green Group 147A. Lower leaf surface: Yellow-Green Group 146A to 146B. Anthocyanin: None observed.

Plant leaves and leaflets:

*Stipules.*—Upper surface: Pubescent. Length: 18 mm. Color: Yellow-Green Group 146A. Shape: Linear with outward extending apecies. Margins: Finely serrated with stipitate glands.

*Petiole.*—Length: 15 to 30 mm. Color: Yellow-Green Group 146C. Diameter: 1 mm.

*Rachis.*—Color: Yellow-Green Group 146C. Length: 40 mm. Texture: Undersides have small prickles.

*Leaflet.*—Edge: Finely serrated. Shape: Generally ovate to rounded with cuspidate apex and rounded base. Texture: Smooth. Arrangement: Odd pinnate. Venation: Reticulate. Glossiness: Moderate. Size: 37 mm (l)×22 mm (w).

Disease resistance: Above average resistance to mildew, rust, black spot, and Botrytis under normal growing conditions in Jackson County, Oreg.

Cold hardiness: The variety 'POULyc004' has been found to be cold tolerant to USDA Cold Hardiness Zone 6.

What is claimed is:

1. A new and distinct variety of rose plant of the climbing rose class, substantially as herein illustrated and described as a distinct and novel rose variety due to its abundant deep yellow flowers, disease resistance, and extended period of bloom.

* * * * *

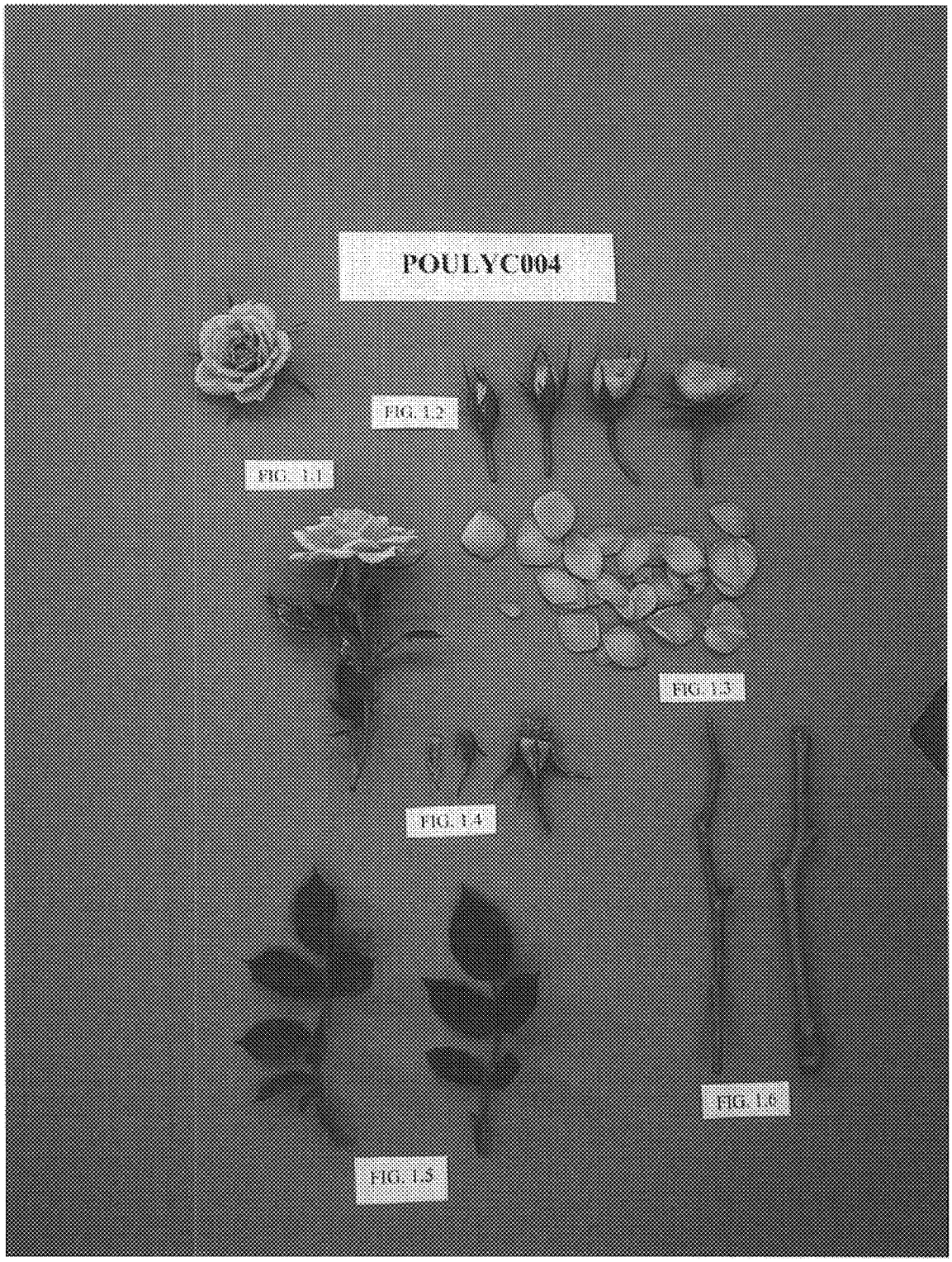
POULYC004
FIG. 1.1
FIG. 1.2
FIG. 1.3
FIG. 1.4
FIG. 1.5
FIG. 1.6